(12) United States Patent
Forsberg et al.

(10) Patent No.: US 8,233,984 B2
(45) Date of Patent: Jul. 31, 2012

(54) EXTERNAL PRESENTATION OF ELECTRICAL STIMULATION PARAMETERS

(75) Inventors: John W. Forsberg, St. Paul, MN (US); Matthew J. Michaels, Glendale, AZ (US); Jeffry C. Palm, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 636 days.

(21) Appl. No.: 12/506,972

(22) Filed: Jul. 21, 2009

(65) Prior Publication Data
US 2009/0281601 A1 Nov. 12, 2009

Related U.S. Application Data

(63) Continuation of application No. 11/222,495, filed on Sep. 8, 2005, now Pat. No. 7,640,059.

(51) Int. Cl.
*A61N 1/08* (2006.01)
(52) U.S. Cl. .............. 607/28; 607/60; 607/63; 600/393
(58) Field of Classification Search .................. 600/393; 607/60, 63, 28
See application file for complete search history.

(56) References Cited

U.S. PATENT DOCUMENTS

| | | |
|---|---|---|
| 4,141,367 A | 2/1979 | Ferreira |
| 4,236,524 A | 12/1980 | Powell et al. |
| 4,638,436 A | 1/1987 | Badger et al. |
| 5,036,850 A | 8/1991 | Owens |
| 5,123,413 A | 6/1992 | Hasegawa et al. |
| 5,183,041 A | 2/1993 | Toriu et al. |
| 5,243,975 A | 9/1993 | Alferness et al. |
| 5,300,096 A | 4/1994 | Hall et al. |
| 5,342,403 A | 8/1994 | Powers et al. |
| 5,370,672 A | 12/1994 | Fowler et al. |
| 5,578,060 A | 11/1996 | Pohl et al. |
| 5,893,883 A | 4/1999 | Torgerson et al. |

(Continued)

FOREIGN PATENT DOCUMENTS

| | | |
|---|---|---|
| WO | WO 97/49455 | 12/1997 |
| WO | WO 2004/004412 | 1/2004 |
| WO | WO 2004/036377 | 4/2004 |

OTHER PUBLICATIONS

Notification of Transmittal of the International Preliminary Report on Patentability, dated Aug. 2, 2007 for corresponding PCT Application No. PCT/US2006/034881, 13 pgs.

(Continued)

*Primary Examiner* — Carl H Layno
*Assistant Examiner* — Natasha Patel
(74) *Attorney, Agent, or Firm* — Shumaker & Sieffert, PA

(57) ABSTRACT

The invention is directed to a trial stimulation system and, more particularly, an indicator device within the trial stimulation system that measures and indicates energy amplitude levels for electrical stimulation therapy delivered to a patient. Specifically, the indicator device simultaneously indicates energy amplitude levels, such as electrical voltage, current, power, and electrical charge, as well as the polarity for each electrode in real-time without affecting the therapy delivered to the patient. For example, the indicator device may activate a number of lights in an array of lights in proportion to the measured energy amplitude level for each electrode and may activate a green LED or a red LED when a corresponding electrodes acts as a source or sink, respectively. In this manner, the indicator device allows a clinician to visualize the electrical fields produced by each electrode and, therefore, may assist stimulation steering, trouble shooting, and lead placement.

34 Claims, 9 Drawing Sheets

U.S. PATENT DOCUMENTS

| | | | |
|---|---|---|---|
| 5,938,690 | A | 8/1999 | Law et al. |
| 6,308,102 | B1 | 10/2001 | Sieracki et al. |
| 6,516,227 | B1 | 2/2003 | Meadows et al. |
| 6,580,948 | B2 | 6/2003 | Haupert et al. |
| 6,609,032 | B1 | 8/2003 | Woods et al. |
| 6,622,048 | B1 * | 9/2003 | Mann et al. .................. 607/46 |
| 6,654,642 | B2 | 11/2003 | North et al. |
| 6,687,538 | B1 | 2/2004 | Hrdlicka et al. |
| 6,907,287 | B1 | 6/2005 | Bevan et al. |
| 6,978,171 | B2 | 12/2005 | Goetz et al. |
| 7,470,236 | B1 | 12/2008 | Kelleher et al. |
| 7,551,960 | B2 | 6/2009 | Forsberg et al. |
| 2002/0007198 | A1 | 1/2002 | Haupert et al. |
| 2002/0183805 | A1 | 12/2002 | Fang et al. |
| 2003/0088289 | A1 | 5/2003 | Levine et al. |
| 2003/0120324 | A1 | 6/2003 | Osborn et al. |
| 2003/0208246 | A1 | 11/2003 | Kotlik et al. |
| 2004/0059395 | A1 | 3/2004 | North et al. |
| 2004/0098063 | A1 | 5/2004 | Goetz |
| 2004/0116978 | A1 | 6/2004 | Bradley |
| 2004/0158119 | A1 | 8/2004 | Osorio et al. |
| 2005/0033386 | A1 | 2/2005 | Osborn et al. |
| 2005/0085743 | A1 * | 4/2005 | Hacker et al. ............. 600/554 |
| 2005/0113887 | A1 | 5/2005 | Bauhahn et al. |
| 2005/0245991 | A1 | 11/2005 | Faltys et al. |
| 2006/0161214 | A1 | 7/2006 | Patel |
| 2006/0241721 | A1 | 10/2006 | Kothandaraman et al. |

OTHER PUBLICATIONS

Office Action dated Aug. 7, 2008 for U.S. Appl. No. 11/222,501 (8 pgs.).

Response dated Nov. 5, 2008 for U.S. Appl. No. 11/222,501 (8 pgs.).

Notice of Allowance dated Feb. 12, 2009 for U.S. Appl. No. 11/222,501 (3 pgs.).

U.S. Appl. No. 11/222,495, filed Sep. 8, 2005, "External Presentation of Electrical Stimulation Parameters,".

Office Action dated Jul. 12, 2007 for U.S. Appl. No. 11/222,495 (11 pgs.).

Responsive Amendment dated Nov. 12, 2007 for U.S. Appl. No. 11/222,495 (24 pgs.).

Office Action dated Jan. 24, 2008 for U.S. Appl. No. 11/222,495 (12 pgs.).

Response dated Apr. 24, 2008 for U.S. Appl. No. 11/222,495 (22 pgs.).

Office Action dated May 28, 2008 for U.S. Appl. No. 11/222,495 (12 pgs.).

Responsive Amendment dated Aug. 28, 2008 for U.S. Appl. No. 11/222,495 (30 pgs.).

Office Action dated Nov. 26, 2008 for U.S. Appl. No. 11/222,495 (12 pgs.).

Request for Continued Examination and Responsive Amendment dated Feb. 24, 2009 for U.S. Appl. No. 11/222,495 (28 pgs.).

Notification of Transmittal of the International Search Report and the Written Opinion of the International Searching Authority, or the Declaration, dated Feb. 9, 2007 for corresponding PCT Application No. PCT/US2006/034881 (15 pgs.).

Reply to Written Opinion dated May 17, 2007 for corresponding PCT Application No. PCT/US2006/034881 (16 pgs.).

* cited by examiner

EXTERNAL PRESENTATION OF ELECTRICAL STIMULATION PARAMETERS

This application is a continuation of U.S. patent application Ser. No. 11/222,495, filed Sep. 8, 2005, now U.S. Pat. No. 7,640,059 the entire content of which is incorporated herein by reference.

TECHNICAL FIELD

The invention relates to medical devices and, more particularly, medical devices for delivery of electrical stimulation therapy via implanted electrodes.

BACKGROUND

Implantable medical devices are used to deliver neurostimulation therapy to patients to treat a variety of symptoms or conditions such as chronic pain, tremor, Parkinson's disease, epilepsy, incontinence, sexual dysfunction, obesity, or gastroparesis. Neurostimulation may involve delivery of electrical pulses via one or more leads that include electrodes located proximate to the spinal cord, pelvic nerves, or stomach, or within the brain of a patient.

Prior to implantation of a neurostimulation device, the patient may engage in a trial period, in which the patient receives an external trial neurostimulation device on a temporary basis. An external trial stimulator screener, for example, may be coupled to one or more implanted leads via a percutaneous lead extension. The trial neurostimulation permits a clinician to observe neurostimulation efficacy and determine whether implantation of a chronic neurostimulation device is advisable.

Specifically, the trial neurostimulation period may assist the clinician in selecting values for a number of programmable parameters in order to define the neurostimulation therapy to be delivered to a patient. For example, the clinician may select an amplitude, which may be current- or voltage-controlled, and pulse width for a stimulation waveform to be delivered to the patient, as well as a rate at which the pulses are to be delivered to the patient. In addition, the clinician also selects particular electrodes within an electrode set on a lead to be used to deliver the pulses, and the polarities of the selected electrodes. A group of parameter values may be referred to as a program in the sense that they drive the neurostimulation therapy to be delivered to the patient.

The clinician may make notations describing a number of programs and feedback perceived from the patient regarding the perceived efficacy of each program. The clinician may then select the "best" program, e.g., a program that the notations indicate is better in terms of clinical efficacy versus side effects than other programs tested.

SUMMARY

In general, the invention is directed to external presentation of electrical stimulation parameters. An external device measures and indicates parameters associated with stimulation therapy delivered to a patient by an external stimulator, such as a trial stimulator, or implantable stimulator. In this manner, a clinician is able to monitor stimulation parameters as stimulation therapy is delivered to the patient via one or more implanted leads. The electrical stimulation parameters may include energy amplitude levels, electrode combinations and polarities for stimulation delivered to a patient during a trial period.

Energy amplitude levels can be measured and indicated for each electrode on a lead implanted in a patient. The amplitude levels include electrical voltage, current, and other energy amplitude levels and may be indicated by activating a number of indicator lights within an array of indicators lights in proportion to the measured energy amplitude level or by textually or graphically representing the measured energy amplitude levels via a display device. As an example, the power delivered per stimulation pulse and the electrical charge or Coloumbs delivered per stimulation pulse may be indicated for each electrode within the array. Additionally, the direction of flow of electrical current, i.e., polarity, may be indicated for each of the electrodes within the array. In this manner, the invention allows a clinician operating a trial stimulator to visualize the electrical fields generated around each electrode at the therapy site.

In accordance with the invention, an indicator device may be electrically connected in series with a trial stimulator, e.g., external trial stimulator or other electrical stimulation generator, and electrodes carried by one or more leads implanted in a patient. Each lead includes an array of electrodes, typically four or eight electrodes, implanted in a patient via a percutaneous lead extension. The trial stimulator may be programmed to deliver stimulation therapy to a patient by a clinician via a clinician programmer or other programming device.

In general, the indicator device measures and indicates the electrical voltage, current, and other levels as well as the direction of current through each electrode on a lead. The indicator device includes a measurement circuit to measure the energy amplitude levels delivered to each electrode and an indicator or display elements, such as an array of indicator lights, a light emitting diode (LED) bar graph, and/or a pixelized display, to indicate the measured energy amplitude levels delivered to each electrode. The measurement circuit may be designed to have a negligible effect on the stimulation therapy delivered to the patient and may comprise a set of substantially identical circuits. Each individual circuit measures the energy amplitude levels for a corresponding one of the electrodes and also identifies the corresponding electrode as a cathode or anode.

The measured energy amplitude levels for each electrode may be indicated or displayed simultaneously to the clinician operating the trial stimulator in real-time. For example, the indicator device may activate an LED bar graph in proportion to the measured energy amplitude levels for each electrode on the connected leads. Additionally, the indicator device may activate an indicator light to indicate the polarity of each electrode, e.g., a green indicator light when the corresponding electrode acts as an anode and a red indicator light when the corresponding electrode acts as a cathode. In another example, the indicator device may graphically represent the measured energy amplitude levels and direction of current flow through each electrode in a pixelized display. In any case, the indicator device may indicate the energy amplitude levels for each electrode simultaneously. More specifically, the indicator device may indicate a single energy amplitude level for each of the electrodes simultaneously or may indicate more than one of the energy amplitude levels for each of the electrodes simultaneously. Consequently, the indicator device enables the clinician to visualize the electrical fields generated around each electrode at the therapy site. Thus, the indicator device may enhance visualization of electrical stimulation field direction and assist trouble shooting.

Further, the trial stimulator may receive the measured energy amplitude levels from the indicator device. In this case, the trial stimulator may communicate with a clinician programmer, a computer device, or other programming device to display the measured energy amplitude levels to the clinician. Alternatively, the trial stimulator may store or archive the measured energy amplitude levels received from the indicator device. A device in communication with the trial stimulator, such as a clinician programmer, computer device, or other programming device, may also store or archive the measured energy amplitude levels received from the indicator device. In any case, the archived energy amplitude levels may be examined, for example, with feedback perceived from the patient to analyze the efficacy of the therapy and optimize, improve, or tailor the neurostimulation therapy over time.

The measured energy amplitude levels received from the indicator device may also be used to control therapy delivered to the patient. For example, the received energy amplitude levels may be compared to values stored in the trial stimulator to control therapy delivered to the patient. By comparing the measured energy amplitude levels to values stored in the trial stimulator, excessive or insufficient stimulation may be prevented from being delivered to a patient. As a result, therapy delivered to the patient may be better controlled, thereby reducing the pain experienced by the patient or enhancing efficacy.

In one embodiment, the invention is directed to a method comprising measuring energy amplitude levels delivered to an array of implanted stimulation electrodes and indicating the measured energy amplitude levels delivered to respective electrodes within the array.

In another embodiment, the invention is directed to a device comprising a measurement circuit that measures energy amplitude levels delivered to an array of implantable stimulation electrodes and an indicator that indicates the measured energy amplitude levels delivered to respective electrodes within the array.

In another embodiment, the invention is directed to a system comprising an electrical stimulation generator that generates stimulation energy, an array of stimulation electrodes coupled to the electrical stimulation generator, a switching circuit to apply the stimulation energy to selected electrodes within the array of electrodes, a measurement circuit that measures energy amplitude levels delivered to the electrodes, and an indicator that indicates the measured energy amplitude levels delivered to respective electrodes within the array.

The invention may provide a number of advantages. For example, measuring energy amplitude levels for each electrode in real-time and indicating the measured energy amplitude levels for each electrode simultaneously allows the clinician to visualize the electrical fields generated around each electrode at the therapy site. Visualization of stimulation steering may facilitate selection of electrode combinations by the clinician. In addition, because the clinician can visualize the electrical fields generated by each electrode, the indicator device may enable the clinician to efficiently determine if the trial stimulator and leads are operating properly as well as diagnose a failure in the trial stimulator or leads. Further, the indicator device may aid in lead placement because the indicator device allows the clinician to visualize the electric field generated by each electrode as the leads are positioned within the patient. Consequently, the clinician can see how the electric fields for each electrode are affected, particularly for cross stimulation, as two or more leads are positioned relative to one another.

The indicator device may also enable the trial stimulator to better control delivery of stimulation therapy. The trial stimulator may compare measured energy amplitude levels received from the indicator device to values stored in local memory and adjust the stimulation delivered to the patient based on the comparison. As a result, excessive or insufficient stimulation may be prevented from being delivered to the patient thereby reducing the pain experienced by the patient or enhancing efficacy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
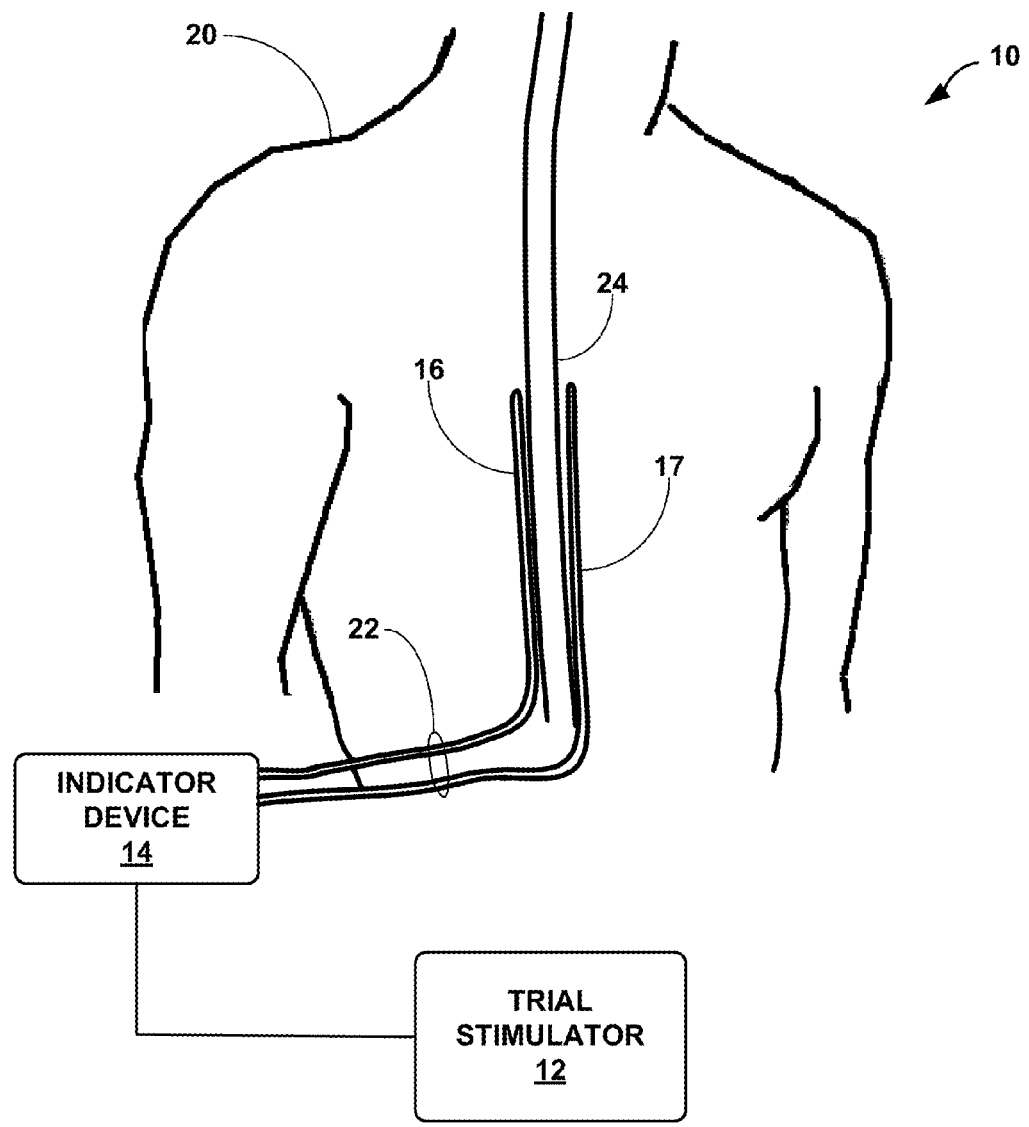
FIG. 1 is a block diagram illustrating an example system for measuring and indicating energy amplitude levels for neurostimulation therapy delivered to a patient in accordance with the invention.

FIG. 1 is a diagram illustrating a trial stimulation system 10 for measuring and indicating energy amplitude levels of electrical stimulation delivered to a patient 20. In FIG. 1, for purposes of illustration, system 10 is configured for spinal cord stimulation. However, system 10 may be adapted for a variety of therapies, including spinal cord stimulation, deep brain stimulation, gastrointestinal tract stimulation, pelvic floor stimulation, and muscle stimulation. In addition, system 10 may deliver therapies designed to alleviate a variety of disorders, such as chronic pain, movement disorders, gastrointestinal disorders, such as gastroparesis and obesity, and pelvic floor disorders such as pelvic pain, incontinence or sexual dysfunction. Accordingly, the application of system 10 to spinal cord stimulation in the example of FIG. 1 is for purposes of illustration and should not be considered limiting of the invention as broadly embodied and described in this disclosure.

As shown in FIG. 1, system 10 includes a trial stimulator 12, an indicator device 14, and implantable leads 16 and 17. Leads 16 and 17 each carry an array of stimulation electrodes (not shown) that are tunneled into patient 20 via a percutaneous port 22. Percutaneous port 22 may be a surgically opened site in the skin to provide passage for leads 16 and 17 to enter patient 20. In the illustrated example, leads 16 and 17 are deployed proximate the spinal cord 24 of patient 20 for delivery of spinal cord stimulation, e.g., for alleviation of chronic pain. For spinal cord, gastrointestinal, or pelvic floor stimulation, as examples, percutaneous port 22 may be located near the lower abdomen or lower back of patient 20, and may be kept open and protected through the use of a ring type seal structure. Alternatively, the skin around percutaneous port 22 may be allowed to close directly around electrical leads 16 and 17. In either case, percutaneous port 22 may physically limit the period of time a patient may use trial stimulator 12.

Leads 16 and 17 are flexible, electrically insulated from body tissues, and terminated with electrodes at the distal ends of the leads. The proximal ends of leads 16 and 17 conduct stimulation pulses generated by trial stimulator 12 to patient 20. Accordingly, leads 16 and 17 are connected in series with indicator device 14 and trial stimulator 12. In some embodiments, one electrical lead or more than two electrical leads may be used to deliver stimulation to patient 20.

In accordance with the invention, trial stimulator 12 delivers electrical stimulation to patient 20 via leads 16 and 17 and indicator device 14 measures and indicates parameters associated with the electrical stimulation. For example, indicator device 14 may measure and indicate the energy amplitude levels delivered to each electrode carried by leads 16 and 17. Indicator device 14 allows a clinician to visualize the electrical fields generated around each electrode at the therapy site in real-time. In particular, indicator device 14 provides a visual or graphical representation of the measured energy amplitude levels for each electrode carried by leads 16 and 17 in real-time. Consequently, the clinician can visualize the electrical field generated by each of the electrodes carried by leads 16 and 17 simultaneously.

Trial stimulator 12 delivers electrical stimulation in the form of electrical pulses according to one or more stimulation programs that define applicable stimulation parameters, such as amplitude, pulse width, pulse rate, and electrode combinations and polarities. A clinician or patient 20 may operate an external programmer (not shown) to select particular programs or parameter values applied by trial stimulator 12. The external programmer communicates with trial stimulator 12 by wired or wireless communication and may have a simple user interface, such as a button or keypad, and a display or lights. In general, the external programmer may be a handheld device configured to permit activation of stimulation and adjustment of stimulation parameters as well as being capable of turning stimulation on or off. In some embodiments, trial stimulator 12 may include a series of buttons, switches, or a small display located on trial stimulator 12. In this case, an external programmer may not be needed to program trial stimulator 12 or an external programmer may be used in addition to the controls located on trial stimulator 12.

In any case, trial stimulator 12 delivers electrical stimulation to patient 20 in accordance with one or more programs. A clinician uses the external programmer to select programs to identify which electrodes carried on leads 16 and 17 deliver the electrical pulses and the polarities of the selected electrodes as well as the voltage or current amplitudes, pulse widths, and pulse rates of the stimulation therapy. Accordingly, indicator device 14 may be configured to measure and indicate electrical voltage, current, and energy amplitude levels and also identify the polarity of each electrode carried by leads 16 and 17. In particular, indicator device 14 may measure and indicate the power delivered per stimulation pulse and the electrical charge or Coulombs delivered per stimulation pulse for each electrode carried by leads 16 and 17. Indicator device 14 indicates the measured energy amplitude levels by, for example, activating a number of indicator lights within an array of indicator lights, such as a light emitting diode (LED) bar graph, in proportion to the measured energy amplitude levels for each electrode. The polarity of each electrode carried by leads 16 and 17 may be indicated by activating a green light when the corresponding electrode acts as an anode and activating a red light when the corresponding electrode acts as a cathode. Alternatively, indicator device 14 may graphically represent the measured energy amplitude levels and polarity for each electrode via a pixelized display. In this manner, indicator device 14 enables a clinician to visualize the electrical fields generated around each electrode carried by leads 16 and 17 at the therapy site.

Indicator device 14 is designed to have a negligible effect on the therapy delivered to patient 20 and may comprise a set of substantially identical measurement circuits. Each measurement circuit measures the energy amplitude levels for a corresponding one of the electrodes carried by leads 16 and 17 and also identifies the corresponding electrode as a cathode or anode. As a result, the energy amplitude levels for each electrode carried by leads 16 and 17 can be measured in real-time and indicated to the clinician simultaneously. Consequently, indicator device 14 allows the clinician to visualize the electrical fields generated around each electrode carried by leads 16 and 17 at the therapy site without affecting the electrical stimulation delivered to patient 20. Thus, rather than selecting programs that best relieve pain experienced by patient 20 by testing numerous programs and combinations of programs, i.e., selecting the best program by trial and error, the clinician may be able to spend less time selecting one or more best programs by visualizing the stimulation delivered to the therapy site. Indicator device 14 may also aid a clinician to place leads 16 and 17 relative to each other within patient 20 because indicator device 14 allows a clinician to visualize the electrical field generated by each electrode carried by leads 16 and 17. Specifically, indicator device 14 allows the clinician to visualize how the electric field is affected for each electrode, particularly for cross stimulation, as leads 16 and 17 are positioned relative to each other. Additionally, indicator device 14 may enable the clinician to efficiently trouble shoot trial stimulator 12 and leads 16 and 17, i.e., to determine if trial stimulator 12 and leads 16 and 17 are operating properly.

Furthermore, in some embodiments, trial stimulator 12 may receive the measured energy amplitude levels from indicator device 14. Indicator device 14 and trial stimulator may communicate via a wired or wireless connection. For example, indicator device 14 may include telemetry electronics to communicate with trial stimulator 12 using radio frequency (RF) telemetry techniques known in the art. In another example, indicator device 14 and trial stimulator 12 may communicate via a wired connection, such as via a serial communication cable. In any case, trial stimulator 12 may communicate the measured energy amplitude levels to an external programmer for display. Accordingly, in this case, the external programmer may include a pixelized display to indicate the measured energy amplitude levels as well as control the delivery of electrical stimulation to patient 20. Thus, the external programmer may be used in addition to indicator device 14 to indicate the measured electrical amplitude parameters. However, in some embodiments, the measured energy amplitude levels may be displayed only on the external programmer.

Trial stimulator 12 may also store or archive energy amplitude levels received from indicator device 14 or communicate the received energy amplitude levels to the external programmer for remote storage. By storing the measured energy amplitude levels, a clinician may access and examine or analyze the archived energy amplitude levels, for example, with perceived feedback from patient 20, to determine the efficacy of the stimulation therapy before implanting a chronic stimulator. If the therapy is successful, patient 20 may undergo surgery to implant a chronic stimulator. If the trial therapy is unsuccessful, the clinician may alter the trial stimulation, try another type of stimulation therapy, or abandon stimulation therapy.

In another embodiment, trial stimulator 12 may use measured energy amplitude levels received from indicator device 14 to control electrical stimulation delivered to patient 20. For example, trial stimulator 12 may adjust the electrical stimulation delivered to patient 12 based on a comparison of measured energy amplitude levels to stored preset or default values, such as threshold values. The stored values may generally define a range of values that define normal operation or may comprise threshold values that define excessive or insufficient energy amplitude levels. Consequently, when the measured energy amplitude levels are not within the range of normal operation, trial stimulator 12 may adjust the electrical stimulation delivered to patient 20 accordingly, i.e., increase the energy amplitude level when the measured levels are below the range defined by the threshold values and decrease the energy amplitude level when the measured levels are above the range. Comparing the measure energy amplitude levels to threshold values may prevent excessive or insufficient stimulation from being delivered to patient 20. As a result, electrical stimulation delivered to patient 20 may be better controlled, thereby increasing the efficacy of the electrical stimulation delivered to patient 20 and possibly reducing pain experienced by patient 20.

In any case, indicator device 14 may generally be used by a clinician to visualize electrical fields generated by each electrode carried by leads 16 and 17. In one example, indicator device 14 is used during trial or "screening" stimulation to evaluate the likely efficacy of electrical stimulation therapy for patient 20. In this example, the clinician may use indicator device 14 to assist in stimulation steering and selecting programs that best relieve pain experienced by patient 20. In another example, a clinician or technician may use indicator device 14 to verify that trial stimulator 12 and leads 16 and 17 are operating properly. By visually representing the electrical field generated by each electrode carried by leads 16 and 17, a clinician or technician may quickly trouble shoot or determine operational failures for trial stimulator 12.

Because indicator device 14 may ordinarily be used in a clinical or research environment, the housing of indicator device 14 may be constructed for external use. Accordingly, the housing of indicator device 14 may be constructed of materials such as polyurethane, polycarbonate, aluminum, and other durable plastic, polymeric or metal alloy materials sufficient to secure and protect the inner components, i.e., measurement circuits and display elements. In some embodiments, for clinical or research use, the housing may be sized to provide sufficient area for indicating the measured energy amplitude levels for each electrode carried by leads 16 and 17 rather than being sized to be easily transportable. As an example, each of leads 16 and 17 may include up to sixteen electrodes and indicator device 14 may simultaneously display electrical voltage, current, and energy amplitude levels as well as the polarity for each electrode. Thus, indicator device 14 may include as many as sixty-four different display fields. Consequently, indicator device 14 may be larger than a handheld device in embodiments in which indicator device 14 indicates the energy amplitude levels by activating a number of lights within an array of lights or an LED bar graph in proportion to the measured energy amplitude levels. However, in embodiments in which indicator device 14 includes a pixelized display, indicator device 14 may be sized to conform to a handheld device since the pixelized display may present a user interface to graphically represent the measured energy amplitude levels. As an example, the user interface may allow a user to select a desired set of energy amplitude levels for a number of electrodes on leads 16 and 17.

Figure 2:
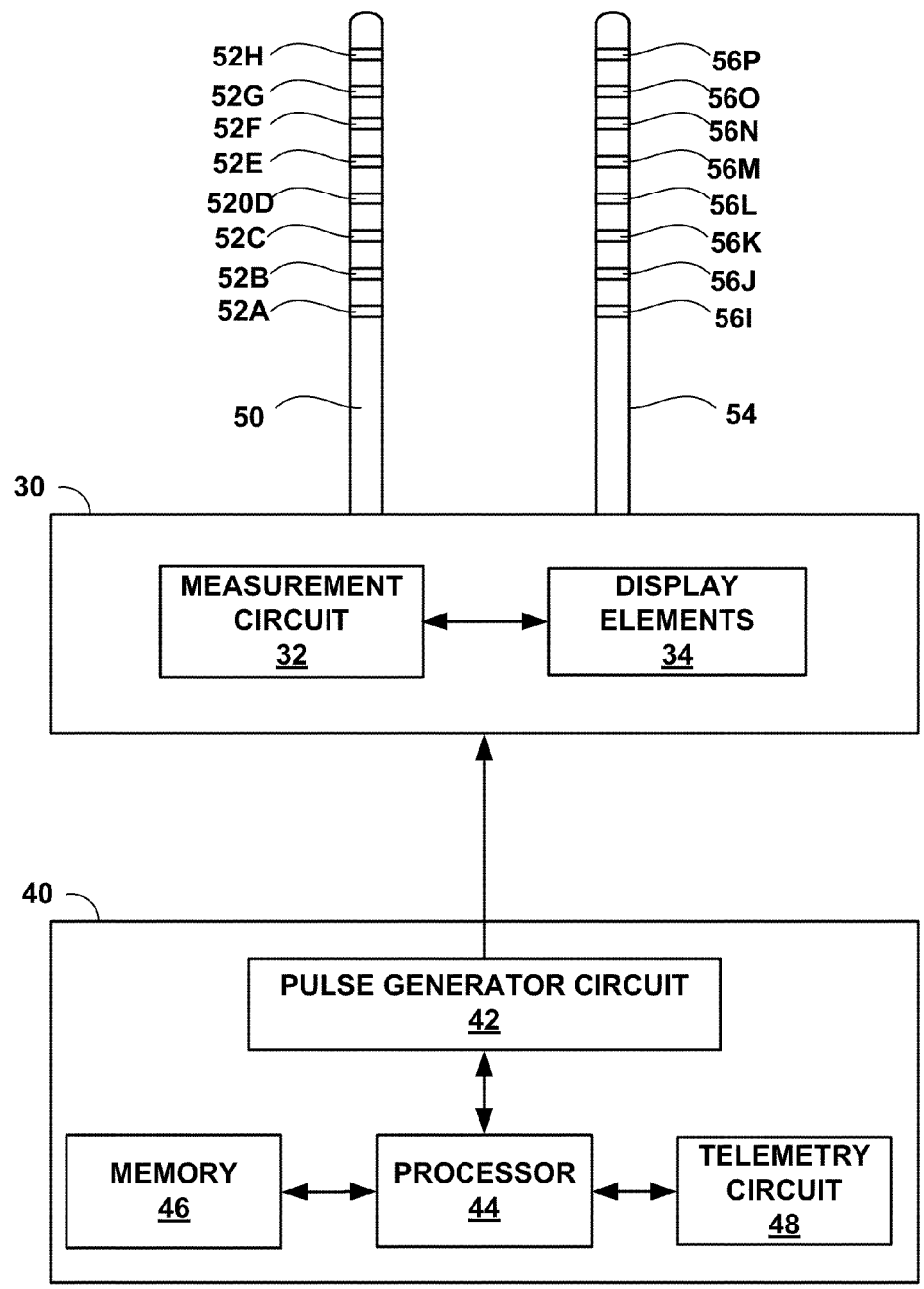
FIG. 2 is a block diagram illustrating an example indicator device connected in series with a trial stimulator and array of stimulation electrodes in accordance with an embodiment of the invention.

FIG. 2 is a block diagram illustrating a configuration of an indicator device 30 electrically connected in series with a trial stimulator 40 and leads 50 and 54. Generally, leads 50 and 54 deliver electrical stimulation in the form of electrical pulses generated by trial stimulator 40 and indicator device 30 measures and indicates the electrical amplitude values of the pulses. Leads 50 and 54 may deliver electrical stimulation therapy via an array of electrodes 52A-H (collectively "electrodes 52") and array of electrodes 56A-H (collectively "electrodes 56"), respectively. Electrodes 52 and 56 may be ring electrodes. Alternatively, electrodes 52, 56 may be constructed as paddle lead electrodes. The configuration, type, and number of electrodes 52 and 56 illustrated in FIG. 2 are merely exemplary.

Electrodes 52 and 56 may be electrically coupled to measurement circuit 32 via leads 50 and 54, respectively, and measurement circuit 32 may be electrically coupled to pulse generator circuit 42. More specifically, measurement circuit 32 is placed in series between electrodes 52 and 56 and pulse generator circuit 42. In this manner, measurement circuit 32 may measure energy amplitude levels delivered to electrodes 52 and 56 via leads 50 and 54, respectively, without substantially affecting the stimulation therapy.

Trial stimulator 40 may include a pulse generator circuit 42, processor 44, memory 46, and telemetry circuit 48. Pulse generator circuit 42 may be coupled to a power source such as a battery (not shown) and may deliver electrical pulses to at least some of electrodes 52 and 56 via leads 50 and 54 under the control of processor 44. Processor 44 controls pulse generator circuit 42 to deliver electrical stimulation therapy according to one or more programs. Specifically, processor 44 may control pulse generator circuit 42 to deliver electrical pulses with electrical voltage, current, and energy amplitude levels and at the pulse widths and rates specified by the selected programs. Processor 44 may also control pulse generator circuit 42 to deliver the pulses via a selected subset of electrodes 52 and 56 with selected polarities, as specified by the selected programs. Processor 44 may control pulse generator circuit 42 to deliver each pulse according to a different program. Processor 44 may include a microprocessor, a controller, a digital signal processor (DSP), an application specific integrated circuit (ASIC), a field programmable gate array (FPGA), discrete logic circuitry, or the like.

Memory 46 may store programs that are available to be selected by a clinician for delivery of electrical stimulation therapy. In some embodiments, memory 46 may also store or record usage information in memory 46. Memory 46 may include any volatile, non-volatile, fixed, removable, magnetic, optical, or electrical media, such as a random access memory (RAM), read-only memory (ROM), compact disc (CD-ROM), hard disk, removable magnetic disk, memory cards or sticks, electrically erasable (EEPROM), flash memory, and the like.

Telemetry circuit 48 allows processor 44 to communicate with an external programmer, such as a clinician programmer or other device suitable for programming trial stimulator 40 during a screening process. Processor 44 may receive programs to test on a patient from the external programmer via telemetry circuit 48 during programming by a clinician. The programs received during programming by a clinician may be stored in memory 46. Telemetry circuit 48 may also allow trial stimulator 40 to communicate with indicator device 30 in embodiments in which trial stimulator 40 receives measured energy amplitude levels from indicator device 30. For example, processor 44 may receive measured energy amplitude levels from indicator device 30 via telemetry circuit 48 and store the received energy amplitude levels in memory 46.

Indicator device 30 includes measurement circuit 32 and display elements 34. Measurement circuit 32 may comprise a set of substantially identical measurement circuits to measure energy amplitude levels of the electrical pulses generated by trial stimulator 40. More specifically, each individual measurement circuit of the set measures the energy amplitude levels, e.g., electrical voltage, current, and other energy amplitude levels, delivered by a corresponding one of electrodes 52 and 56 carried on leads 50 and 54, respectively. As an example, each individual measurement circuit of the set may measure the power delivered per stimulation pulse or the electrical charge or Coulombs delivered per stimulation pulse delivered by a corresponding one of electrodes 52 and 56 carries on leads 50 and 54, respectively. Each individual measurement circuit also identifies the corresponding electrode as a cathode or anode. Consequently, measurement circuit 32 may measure the energy amplitude levels for each of electrodes 52 and 56 in real-time.

Display elements 34 may comprise an array of indicator lights, such as an LED bar graph, or a pixelized display. Where display elements 34 comprise an array of indicator lights, a number of indicator lights may be activated in proportion to the measured energy amplitude levels. In particular, display elements 34 may comprise an array of indicator lights to indicate the measured energy amplitude levels, such as one or more of electrical voltage, current, power delivered per stimulation pulse, electrical charge delivered per stimulation pulse, and other energy amplitude levels, for each of electrodes 52 and 56. Display elements 34 may also comprise separate indicator lights to indicate the polarity of each of electrodes 52 and 56. Thus, display elements 34 enable indicator device 30 to display the measured energy amplitude levels for each of electrodes 52 and 56 simultaneously.

As an example, display elements 34 may include three arrays of indicator lights for each of electrodes 52 and 56 when measurement circuit 32 measures the electrical voltage, current, and energy amplitude levels. In an alternative example, display elements 34 may include a single array of indicator lights for each of electrodes 52 and 56 to indicate a particular one of electrical voltage, current, power delivered per stimulation pulse, and electrical charge delivered per stimulation pulse, and other energy amplitude levels. In this case, indicator device 30 may include a switch to allow a clinician to select which of the energy amplitude levels to be indicated by the array of indicator lights. Display elements 34 may also include a red indicator light and a green indicator light for each of electrodes 52 and 56 to identify the corresponding electrode as an anode or cathode.

Where display elements 34 comprise a pixelized display, the measured energy amplitude levels may be graphically represented by a user interface presented on the pixelized display. The amplitude levels may be presented, for example, as bar graph, pie chart, or other graphical metaphors. Alternatively, the amplitude levels may be presented as numerical values or textual indications, e.g., high, medium, low, anode, cathode. In one example, the user interface may graphically represent the energy amplitude levels for each of electrodes 52 and 56 in a single screen. In another example, the user interface may allow a clinician to select one or more of the measured energy amplitude levels to be displayed for each of a group or an individual one of electrodes 52 and 56.

Indicator device 30 may also include a processor (not shown) and telemetry circuitry (not shown) in some embodiments. For example, where trial stimulator 40 stores measured energy amplitude levels, indicator device may include telemetry circuitry that allows a processor to communicate measured energy amplitude levels to trial stimulator 40.

In an alternative embodiment, indicator device 30 may be integrated with trial stimulator 12. In this case, the combination indicator and trial stimulator device may include telemetry circuitry to communicate measured energy amplitude levels to an external programmer for display to a clinician. Thus, the combination indicator and trial stimulator device may be an external or implanted device.

The measured electrical amplitude parameters may be received from indicator device 30 and stored in memory 46. A clinician may access memory 46 to retrieve and examine the stored energy amplitude levels. The clinician may analyze the stored energy amplitude levels along with patient perceived feedback from the patient to determine the efficacy of the stimulation therapy before implanting a chronic stimulator.

Figure 3:
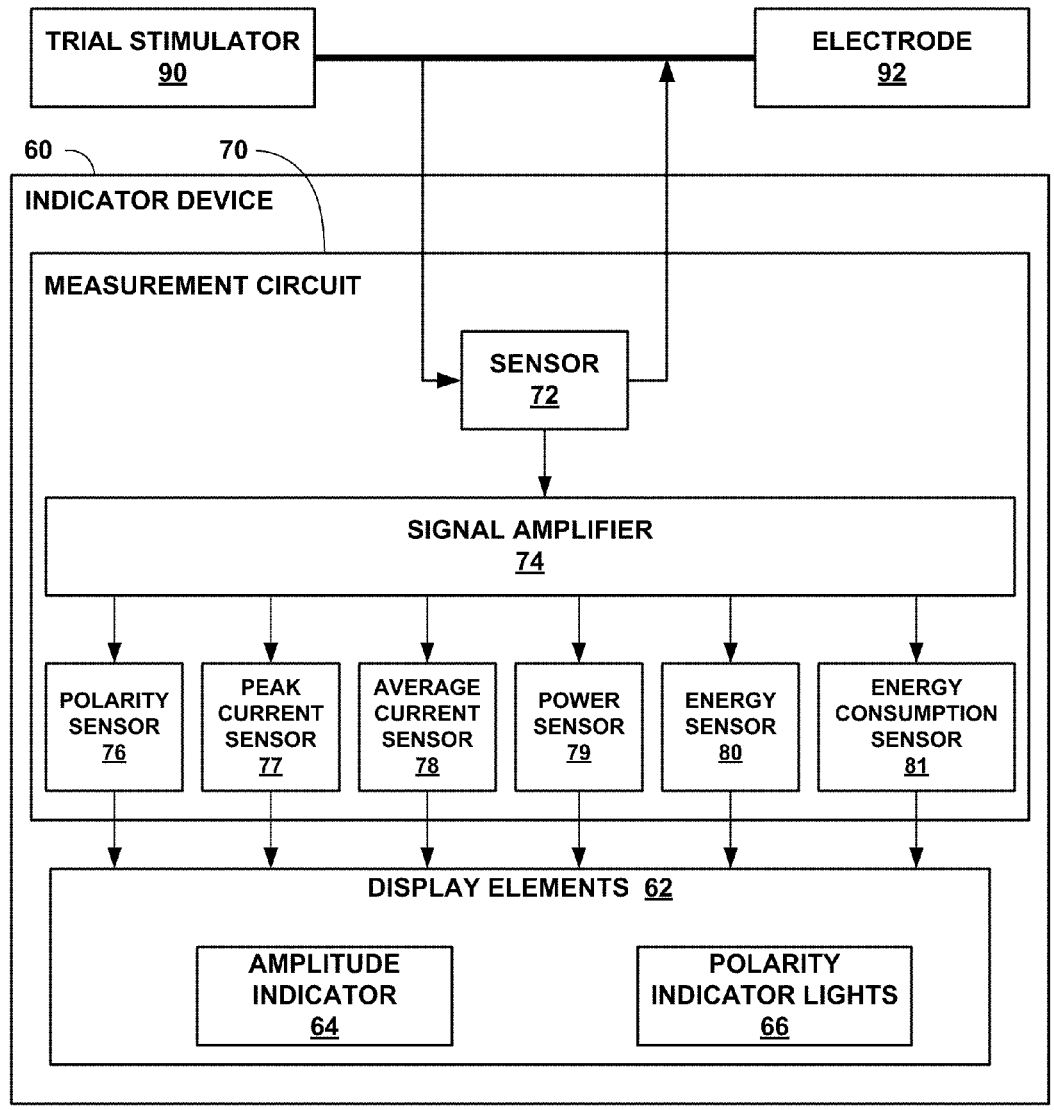
FIG. 3 is a functional block diagram of an indicator device illustrating various components of an exemplary indicator device.

FIG. 3 is a functional block diagram illustrating various components of an exemplary indicator device 60. In general, indicator device 60 measures energy amplitude levels of electrical stimulation pulses generated by trial stimulator 90 and indicates the measured levels to a clinician or other authorized user operating trial stimulator 90 in real-time. In FIG. 3, for purposes of illustration, electrical stimulation pulses are delivered to a patient via a single electrode 92 that may be carried by a lead (not shown) implanted within the patient. Accordingly, indicator device 60 in the example of FIG. 3 includes a single measurement circuit 70 to measure the energy amplitude levels of electrical stimulation pulses delivered by electrode 92. However, trial stimulator 90 may be adapted to deliver electrical stimulation to the patient via more than one lead with each lead carrying an array of electrodes. Where trial stimulator 90 generates electrical stimulation pulses to be delivered to the patient via an array of electrodes, indicator device 60 may include a set of substantially identical measurements circuit with each individual measurement circuit measuring energy amplitude levels for a corresponding electrode in the array of electrodes. As a result, indicator device 60 indicates the measured energy amplitude levels for each of the electrodes simultaneously. Consequently, indicator device 60 is for illustrative purposes and should not be considered limiting of the invention as broadly embodied and described.

As shown in FIG. 3, measurement circuit 70 may include a signal sensor 72, such as a resistor or other circuit element through which a signal may be sensed, a signal amplifier 74, a polarity sensor 76, a peak current sensor 77, an average current sensor 78, a power sensor 79, an energy sensor 80, and an energy consumption sensor 81. Measurement circuit 70 is electrically connected in series between trial stimulator 90 and electrode 92 and is designed to have negligible effect on the stimulation therapy delivered to the patient via electrode 92. More specifically, measurement circuit 70 measures energy amplitude levels across signal sensor 72. When signal sensor 72 is implemented as a resistor, the resistor may have a value of resistance much less than the resistance of electrode 92. Measurement circuit 70 may also include additional circuit elements (not shown) to prevent electrical charge from building up and filter high frequency noise components, such as those produced from cabling, out of the signal received by signal amplifier 74.

Signal amplifier 74 may comprise one or more differential amplifiers or other circuit elements suitable for amplifying the electrical signal across signal sensor 72. The output of signal amplifier 74 may be output to polarity sensor 76, peak current sensor 77, average current sensor 78, power sensor 79, energy sensor 80, and energy consumption sensor 81 (collectively "sensors 76-81"). Polarity sensor 76 may comprise one or more diodes or other circuit components suitable for identifying the direction of current flow through signal sensor 72. Peak current sensor 77 may comprise a hold circuit, such as a resistor and capacitor electrically connected in parallel, that holds the peak voltage. The rate at which the signal decays may be dependent on the capacitance of the capacitor in the hold circuit.

In addition, average current sensor 78 measures the average current through signal sensor 72, for example, by measuring a rectified current output. Energy consumption sensor 81 may comprise an integrator circuit suitable for generating an output signal proportional to the total power consumed by electrode 92 or projected life of trial stimulator 90, respectively. Total energy sensor 80 generates an output signal proportional to the number of Columbs per pulse delivered by electrode 92 and other electrodes electrically connected to trial stimulator 90. Power sensor 79 generates an output signal proportional to the power delivered per pulse by trial stimulator 90 to electrode 92 and other electrodes electrically connected to trial stimulator 90. Accordingly, power sensor 79 receives applied stimulation voltage generated by trial stimulator 90. The applied stimulation voltage may be measured at trial stimulator 90 or provided as a direct input to power sensor 79.

The output of sensors 76-81 is generally proportional to the energy amplitude levels, i.e., electrical voltage, current, power delivered per stimulation pulse, electrical charge delivered per stimulation pulse, and energy amplitude levels, generated by trial stimulator 90 and is received by display elements 62. As a result, display elements 62 indicate the energy amplitude levels delivered by electrode 92 and polarity of electrode 92 via an amplitude indicator 64, such as a ten segment LED or bar graph, and polarity indicator lights 66, respectively. For example, amplitude indicator 64 may include a single ten segment LED to display the measured energy amplitude levels in accordance with an output signal received from one of sensors 76-81 or, alternatively, may include more than one ten segment LED to display measured energy amplitude levels in accordance with output signals received from more than one of sensors 76-81. For example, amplitude indicator 64 may include a set of ten segment LEDs to display the output signal from each of sensors 76-81. By including a set of ten segment LEDs with each ten segment LED receiving the output signal for each of sensor 76-81, the output of all of sensors 76-81 can be indicated simultaneously. Where amplitude indicator 64 includes a single ten segment LED or fewer ten segment LEDs than number of sensors 76-81, indicator device 60 may include a switch or other means that allow the clinician to select which of the sensors 76-81 to display.

In a similar fashion, polarity lights 66 indicate to the clinician the polarity of electrode 92 in accordance with the output received from polarity sensor 76. For example, polarity lights 66 may include a green and a red indicator light, such as an LED. Indicator device 60 may activate the green indicator light when electrode 92 acts as an anode and may activate the red indicator light when electrode 92 acts as a cathode. In embodiments in which electrical stimulation is delivered to the patient via an array of electrodes, polarity indicator lights may include polarity lights for each of the electrodes so as to enable the polarity of each electrode to be displayed simultaneously.

In some embodiments, display elements 62 may include a pixelized display (not shown) in addition to or in place of amplitude indicator 64 and polarity lights 66. The pixelized display may present a user interface with which the clinician may interact to graphically represent the energy amplitude levels and polarity of one or more electrodes in accordance with the output of sensors 76-81. In any case, display elements 62 allow the clinician to visualize the electrical voltage, current, and other amplitude levels generated by electrode 82.

Figure 4:
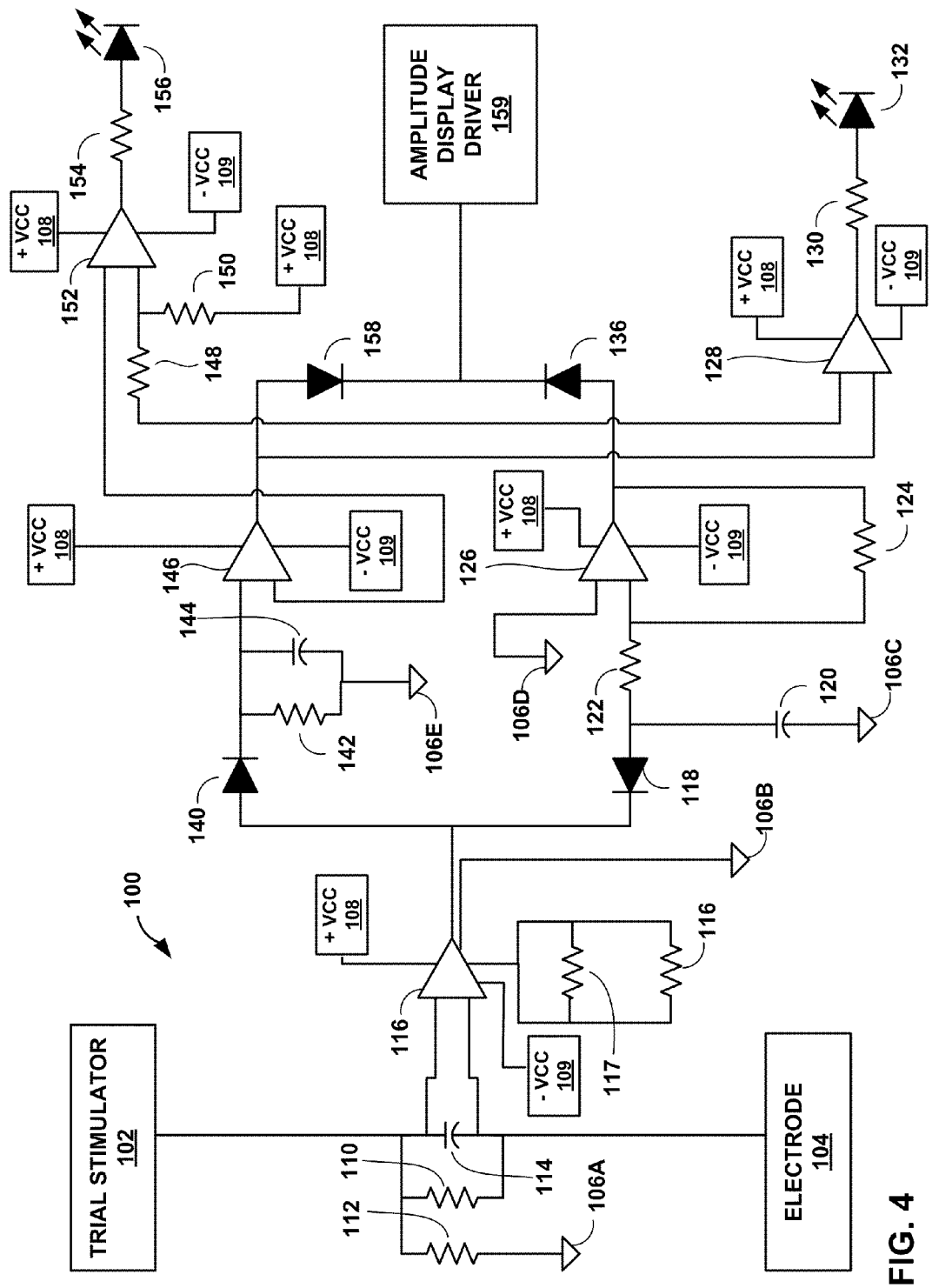
FIG. 4 is a schematic diagram illustrating a circuit in an indicator device that measures energy amplitude levels of electrical stimulation delivered to a patient via an electrode.

FIG. 4 is a schematic diagram illustrating a measuring circuit 100 suitable for use in an indicator device as described. Electrode 104 delivers electrical stimulation pulses to the patient and may comprise one electrode of an array of electrodes carried by a lead implanted within a patient and. Trial stimulator 102 generates the stimulation pulses according to one or more programs selected by a clinician or other authorized user. In general, trial stimulator 102 delivers electrical pulses via a subset of electrodes within an array of electrodes carried by a lead, as specified by the selected programs. In the illustrated example, measuring circuit 100 measures energy amplitude levels of stimulation pulses delivered to a patient via electrode 104 and also identifies electrode 104 as an anode or cathode. Consequently, an indicator device may comprise a set of measuring circuits to measure the energy amplitude levels of stimulation pulses delivered by each electrode. More specifically, each individual measuring circuit may be substantially identical to measuring circuit 100.

Measuring circuit 100 is designed to measure energy amplitude levels, such as electrical voltage, current, and energy amplitude levels, of stimulation pulses delivered to a patient via electrode 104 without substantially affecting the stimulation therapy. Measuring circuit 100 also identifies the polarity of electrode 104. As shown in FIG. 4, the energy amplitude levels are measured across resistor 110. Resistor 110 may have a resistance value much less than the resistance value of electrode 104. As one example, the resistance value of resistor 110 may be approximately 2.5 ohms (Ω). Resistor 112 shares a common node with resistor 110 and is also connected to an equi-potential wire that may serve as a ground for measuring circuit 100. In the illustrated example, resistor 112 is connected to the equi-potential wire at equi-potential node 106A. A number of circuit elements are connected to the equi-potential wire at various other nodes 106B-106E (collectively "equi-potential nodes 106"). Resistor 112 serves to prevent electrical charge from building in measuring circuit 100 and, thus, may have a large resistance value, e.g., 8.2 (mega ohms) MΩ, relative to resistor 110.

Capacitor 114 is connected in parallel with resistor 110 and serves to filter high frequency noise components from the inputs to amplifier 116. Amplifier 116 accepts the electrical signal through resistor 110 and capacitor 114 as an input signal and outputs an amplified signal that can be processed to identify the direction of current and measure the energy amplitude levels of the signal. In particular, the resistive values of resistors 117 and 118 may be selected to specify or set the gain of amplifier 116. As shown in FIG. 4, the positive and negative power inputs of amplifier 116 are electrically connected to power supply rails +VCC 108 and −VCC 109. The positive and negative power inputs of amplifiers 126, 146, 128, and 152 are also connected to +VCC 108 and −VCC 109. Generally, measuring circuit 100 may be connected to a single power source that supplies +VCC 108 and −VCC 109.

Diodes 140 and 118 receive the electrical signal output by amplifier 116 and serve to identify the direction of current of the electrical signal. As an example, suitable commercially available diodes for use as diodes 140 and 118 are SD103A diodes, manufactured by Diodes Incorporated, of West Lake Village, Calif. As illustrated in FIG. 4, diode 140 conducts the electrical signal when electrode 104 acts as a source and diode 118 conducts the electrical signal when electrode 104 acts as a sink. Consequently, the electrical signal may only be conducted along one path, i.e., the upper path through diode 140 or lower path through diode 118. When electrode 104 acts as a source, capacitor 144 and resistor 142 are connected in parallel to form a hold circuit that holds the peak voltage of the electrical signal. The rate at which the electrical signal decays from the hold circuit is dependent on the capacitive value of capacitor 142. In the illustrated example, capacitor 142 and resistor 144 have capacitive and resistive values of 0.1 micro Farads (µF) and 2.2 MΩ, respectively, and have a common equi-potential node 160E.

The electrical signal is then processed by a voltage follower circuit 146 that may comprise an instrumentation amplifier. Voltage follower circuit 146 acts as a buffer and provides a high input impedance, low output impedance, and unity gain. The output of voltage follower circuit 146 is used as an input to amplitude display driver 159. Amplitude display driver 159 may comprise a ten segment LED driver. The output of voltage follower 146 drives amplitude display driver 159 when electrode 104 acts as a source because diode 158 conducts the electrical signal and diode 136 acts as an open circuit. When implemented as a ten segment LED display driver, amplitude display driver 159 actives a number of LEDs in an array of 10 LEDs (not shown) in proportion to the electrical signal. For example, amplitude display driver 159 may output a signal to a ten segment LED bar graph that activates a number of LEDs in proportion to the electrical voltage, current, power delivered per stimulation pulse, electrical charge delivered per stimulation pulse, or other energy amplitude level of the signal. More specifically, amplitude display driver 159 may activate a number of LEDs in a ten-segment LED bar graph in proportion to the peak current, average current, power delivered per stimulation pulse, electrical charge delivered per stimulation pulse, energy consumed by electrode 104, or projected life of trial stimulator 102.

In addition, the output of voltage follower 146 is used as an input for amplifier circuit comprising instrumentation amplifier 152 and resistors 148 and 150. More specifically, the output of voltage follower 146 is supplied to the non-inverting input of amplifier 152 and the inverting input of amplifier 152 is driven by a +VCC power source 108 through resistors 148 and 150. Thus, resistor 154 may be selected to control the voltage of the electrical signal output by the amplifier to activate LED 156 thereby identifying electrode 104 as a source. LED 156 may comprise a green LED so that, when activated, LED 156 identifies electrode 104 as an anode, i.e., a positive polarity electrode.

Where electrode 104 acts as a cathode, i.e., a negative polarity electrode, diode 118 conducts the output of amplifier 116 and diode 140 acts as an open circuit. In this case, resistor 122 and capacitor 120 form a hold circuit to hold the peak voltage of the electrical signal and may have resistive and capacitive values similar to resistor 142 and capacitor 144, i.e., 2.2 MΩ and 0.1 µF, respectively. The rate at which the electrical signal decays is dependent on the capacitive value of capacitor 120.

The electrical signal is then processed by the inverting amplifier formed by amplifier 126 and resistor 124. Specifically, the electrical signal output by amplifier 126 is inverted, i.e., the polarity of the signal is reversed, and scaled or amplified based on the resistive value of resistor 124. Resistor 124 may have a resistive value of 2.2 MΩ. The electrical signal output by amplifier 126 is used as the input to amplitude display driver 159 because diode 158 acts as an open circuit and diode 136 conducts the electrical signal in this case. As previously described, amplitude display driver 159 outputs a signal that may activate a number of lights in a ten-segment LED bar graph in proportion to the energy amplitude levels delivered to electrode 104. For lower energy amplitude levels, a lesser number of LEDs is illuminated. For higher energy amplitude levels, a greater number of LEDs is illuminated. The number of illuminated LEDs varies between zero and all LEDs in dependence on the measured amplitude level.

The output of amplifier 126 is also used as an input for amplifier 128 that drives LED 132. LED 132 may comprise a red LED so that, when activated, LED 132 identifies electrode 104 as an anode. In particular, non-inverting input of amplifier 128 is supplied with +VCC 108 voltage through resistors 150 and 148. Resistor 130 is selected to control the voltage of the signal output by amplifier 126. The electrical signal output by amplifier 126 drives LED 132 through resistor 130 and activates LED 132 when electrode 104 acts as a sink. Consequently, measuring circuit 100 enables a clinician to visualize the polarity of electrode 104 and the electrical fields generated by electrode 104.

Figure 5:
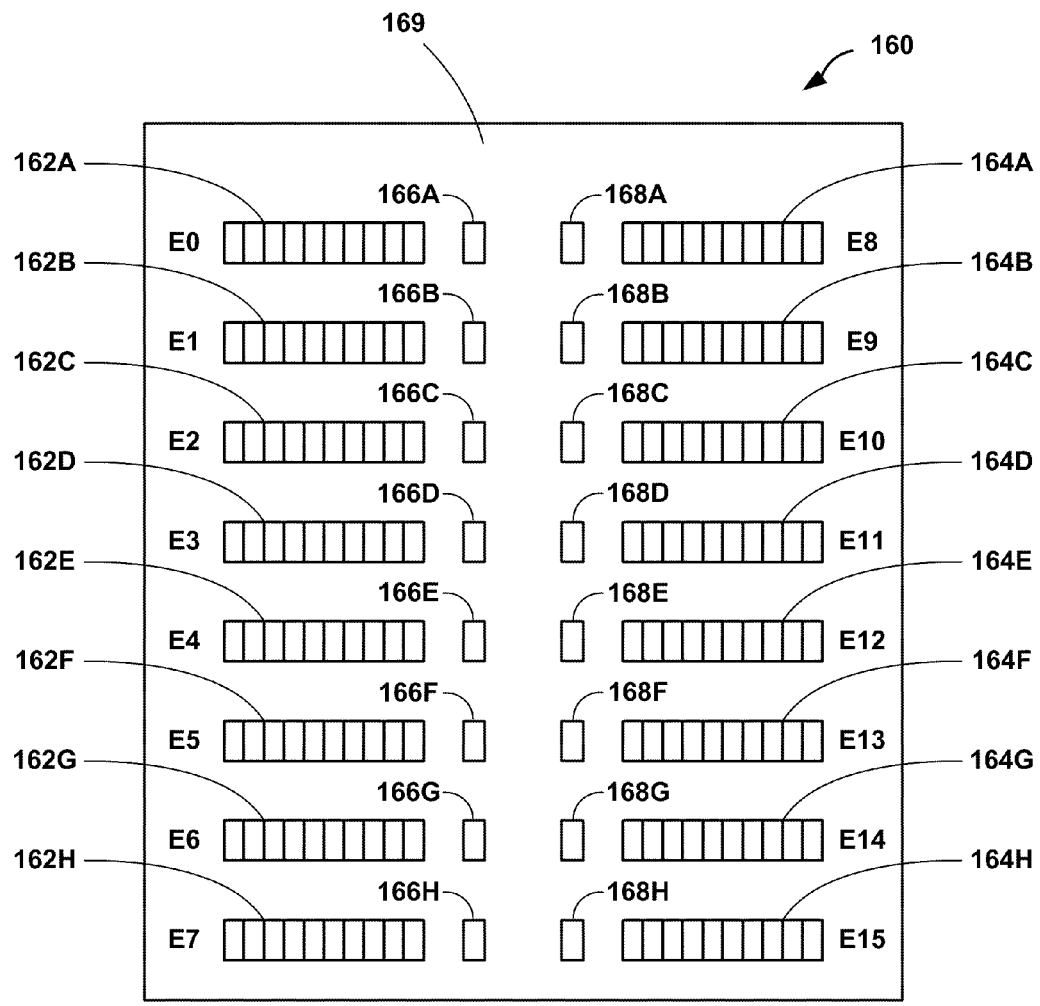
FIG. 5 is a diagram illustrating an exemplary embodiment of an indicator device in accordance with an embodiment of the invention.

FIG. 5 is a schematic diagram illustrating an exemplary indicator device 160 for measuring and indicating energy amplitude levels delivered to a patient. In general, indicator device 160 may be electrically connected in series with a trial stimulator (not shown) and one or more leads (not shown) implanted within a patient during a trial period. Accordingly, indicator device 160 may include electrical ports for receiving a wire or cable to electrically connect to a trial stimulator and one or more medical leads. During the trial period, the trial stimulator delivers electrical stimulation therapy according to one or more programs selected by the clinician. The clinician evaluates the efficacy of the therapy and determines whether implantation of a chronic stimulation device is advisable. Indicator device 160 enables the clinician to visualize the electrical fields produced by each electrode carried by the leads and, therefore, may assist stimulation steering and trouble shooting.

More specifically, indicator device 160, as shown in FIG. 5, may be particularly suitable for trial stimulation systems comprising a trial stimulator that delivers electrical stimulation therapy to a patient via two leads implanted within the patient that each carry an array of eight electrodes implanted within a patient. Accordingly, indicator device includes ten segment LED bar graphs 162A-H (collectively "ten segment LED bar graphs 162") and ten segment LED bar graphs 164A-H (collectively "ten segment LED bar graphs 164") for indicating the measured energy amplitude levels for each electrode carried by the first and second lead, respectively. The electrodes carried by the first lead are designated electrodes E0-E7 and the electrodes carried by the second lead are designated electrodes E8-E15. In any case, the number of LEDs activated in LED bar graphs 162 and 164 are proportional to the energy amplitude level of electrical stimulation delivered by the corresponding electrodes. For example, LED bar graph 162A indicates the energy amplitude level, such as an electrical voltage, current, power delivered per stimulation pulse, or electrical charge delivered per stimulation pulse by electrode E0. Accordingly, when electrode E0 delivers an stimulation pulse with maximum current, all the LEDs of LED bar graph 162A are activated. In contrast, when electrode E0 delivers an electrical stimulation pulse with minimum current, only a single LED of LED bar graph 162A is activated, e.g., the LED closest to polarity light 166A.

In addition, indicator device 160 includes indicator lights 166A-166H (collectively "indicator lights 166") and indicator lights 168A-H (collectively "indicator lights 168") to identify the polarity of each of electrodes E0-E15. When one of electrodes E0-E15 acts as an anode, the corresponding one of indicator lights 166 and 168 may indicate such by activating a green LED. In contrast, indicator lights 166 and 168 may activate a red LED when the corresponding electrodes E0-E15 act as a cathode.

Each of LED bar graphs 162 and 164 may indicate the same energy amplitude level, such as the electrical voltage amplitude level, for each of electrodes E0-E15 or, alternatively, indicator device 160 may be designed to allow a clinician or other authorized user to select one of a number of energy amplitude levels to indicate for electrodes E0-E15 on an individual basis. As an example, each of LED bar graphs 162 and 164 may indicate one of the electrical voltage, current, power delivered per stimulation pulse, electrical charge delivered per stimulation pulse, or other energy amplitude of electrical stimulation delivered via the corresponding one of electrodes E0-E15. As another example, in accordance with FIG. 3, LED bar graphs 162 and 164 may indicate one of the peak current, average current, power delivered per stimulation pulse, and electrical charge delivered per stimulation pulse by electrodes E0-E15. In addition, indicator device 160 may also include additional LED bar graphs (not shown) to indicate the total or overall power delivered per pulse by electrodes E0-E15 collectively and the projected life or power remaining for the trial stimulator.

In operation, electrodes E0-E15 may deliver electrical stimulation according to multiple programs at substantially the same time in order to address the symptoms of a patient more completely. For example, electrodes E0-E15 may deliver each stimulation pulse according to a different program. Thus, a series of N pulses may deliver therapy according to N different programs and evaluating programs may become complex. However, indicator device 160 allows a clinician to visualize electrical fields and, more specifically, energy amplitude levels, and the pulse rates and other temporal information for electrical stimulation delivered by electrodes E0-E15. In particular, LED bar graphs 162 and 164 enable a clinician to visualize the electrical fields generated by electrodes E0-E15 concurrently and in real-time. In this manner, indicator device 160 may allow a clinician to better select programs to more completely treat the symptoms of the patient. Indicator device 160 may also aid in lead placement because LED bar graphs 162 and 164 allow the clinician to visualize how the electric fields for each electrode are affected, particularly for cross stimulation, as two or more leads are positioned relative to one another. In addition, indicator device 160 may allow a clinician or technician to more efficiently troubleshoot or identify a problem in a trial stimulation system when the system is not operating properly.

As shown in FIG. 5, indicator device 160 is configured to measure and indicate energy amplitude levels for electrical stimulation delivered to a patient via sixteen electrodes, such as for a two-lead configuration with eight electrodes disposed on each lead. However, indicator device 160 may be adapted to measure and indicate energy amplitude levels for electrical stimulation therapy delivered to a patient via a variety of lead configurations, such as a single configuration or a configuration comprising more than two leads, having an array of 16 electrodes or 4 leads each having an array of 4 electrodes and other lead configurations. In each of these configurations, ten segment LED bar graphs 162A and 164A may indicate a measured energy amplitude level for the corresponding electrode and indicator lights 166 and 168 may identify the polarity for the corresponding electrode because there is a one-to-one correspondence between electrodes and ten segment LED bar graphs 162 and 164 and indicator lights 166 and 168.

In general, indicator device 160 may be designed to include any number of ten segment LED bar graphs and polarity lights so as to ensure a one-to-one correspondence with the number of electrodes on leads delivering electrical stimulation to a patient. However, indicator device 160 may also be designed to indicate multiple energy amplitude levels for each electrode as well as the polarity for each electrode. For example, indicator device 160 may be designed to include multiple LED bar graphs for each electrode in order to display multiple energy amplitude levels, such as voltage, current, powered delivered per pulse, and electrical charge delivered per puse for each of the electrodes in the trial stimulation system. Indicator device 160 may also be designed to indicate energy amplitude levels and polarities for configurations with a lesser number of electrodes than ten segment LED bar graphs and indicator lights. Accordingly, the application of indicator device 160 in a trial stimulation system in the example of FIG. 5 is for purposes of illustration and should not be considered limiting of the invention as broadly embodied and described.

As described previously, housing 169 of indicator device 160 may be constructed for external use because indicator device 160 may ordinarily be used in a clinical or research environment. Housing 169 may generally be sized to provide sufficient area for LED bar graphs 162 and 164 and indicator lights 166 and 168. Consequently, indicator device 160 may be sized larger than a handheld device in embodiments in which housing 169 is sized to accommodate a large number of LED bar graphs and indicator lights. However, indicator device 160 may include a pixelized display (not shown) that presents a user interface to graphically represent the measured energy amplitude levels for electrodes E0-E15. In such embodiments, housing 169 may be sized to conform to a handheld device because the pixelized display may graphically represent the energy amplitude levels in a space efficient manner.

Figure 6:
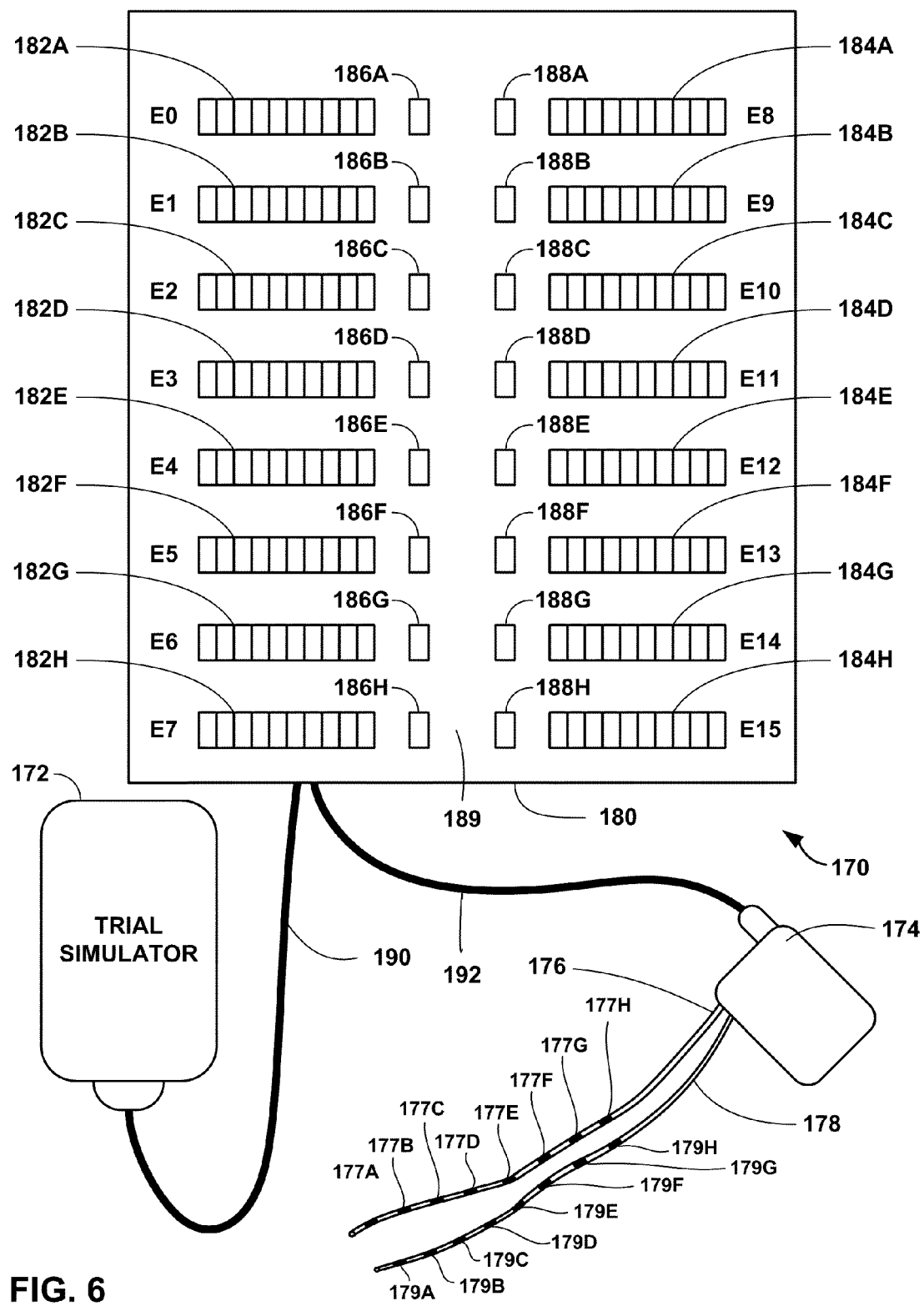
FIG. 6 is a diagram illustrating an example system for measuring and indicating energy amplitude levels delivered to electrodes on medical leads.

FIG. 6 is a diagram illustrating an trial stimulation system 170 that allows a clinician or other authorized user to concurrently visualize electrical fields generated by each of electrodes 177A-H (collectively "electrodes 177") and 179A-H (collectively "electrodes 179") disposed on leads 176 and 178, respectively, in real-time. Trial stimulation system 170 may be used to evaluate the likely efficacy of electrical stimulation for a patient prior to implantation of a chronic stimulator. For example, trial stimulation system 170 may be used for a short time, e.g., a period of hours, days, or weeks, after which the patient and clinician are able to determine if the stimulation therapy is effective in alleviating the symptoms of the patient. If the therapy is successful, the patient may undergo surgery to implant a chronic stimulator. If the trial therapy is unsuccessful, the physician may alter the trial stimulation, try another type of stimulation therapy, or abandon stimulation therapy.

Trial stimulation system 170 comprises a trial stimulator 172, an indicator device 180, and leads 176 and 178 electrically connected to connector block 174 and functions in a similar manner as previously described with respect to trial stimulation system 10. Trial stimulator 172 may comprise an external trial stimulator and generates electrical stimulation in the form of electrical pulses according to one or more programs selected by a clinician. In particular, a clinician may select particular programs by operating an external programmer (not shown), such as a clinician programmer or other suitable programming device. In some embodiments, trial stimulator 172 may include a series of buttons, switches, or a small display with which a clinician may interact to select programs or adjust stimulation parameters for selected programs.

Leads 176 and 178 carry electrodes 177 and 179, respectively, and may be tunneled into a patient (not shown) via a percutaneous port. For example, the percutaneous port may be located near the lower abdomen or lower back of the patient and leads 176 and 178 may be deployed proximate to the spinal cord of a patient for delivery of spinal cord stimulation, e.g., for alleviation of chronic pain. As shown in FIG. 6, electrodes 177 and 179 are located on the distal ends of leads 176 and 178, respectively, and may be flexible and electrically insulated from body tissue. The proximal ends of leads 176 and 178 are electrically connected to connector block 174 and conduct stimulation pulses generated by trial stimulator 172. Connector block 174 provides easy connection and access to leads 176 and 178. In particular, if the trial stimulation is successful, the clinician may implant a chronic stimulator, but before implanting the chronic stimulator disconnects leads 176 and 178 from connector block 174 and connects leads 176 and 178 to the chronic stimulator.

Trial stimulator 172 and connector block 174 may be connected to indicator device 180 via wires or cables 190 and 192, respectively. Accordingly, trial stimulator 180 may include ports for receiving wires 190 and 92. In any case, indicator device 180 is electrically connected in series with trial stimulator 172 and connector block 174. Thus, indicator device 180 may measure and indicate energy amplitude levels for electrical stimulation delivered by each of electrodes 177 and 179 without affecting the electrical stimulation delivered to the patient.

Indicator device 180 may operate and be constructed substantially identically to indicator device 160 of FIG. 5. Accordingly, indicator device 180 includes ten segment LED bar graphs 182A-H (collectively "ten segment LED bar graphs 182") and ten segment LED bar graphs 184A-H (collectively "ten segment LED bar graphs 184") for indicating the measured energy amplitude levels for each of electrodes 177 and 179. Electrodes 177A-H are labeled as electrodes E0-E7 and electrodes 1779A-H are labeled as electrodes E8-E15 on indicator device 180. Indicator device 180 also includes indicator lights 186A-H (collectively "indicator lights 186) and indicator lights 188A-H (collectively "indicator lights 188") to identify the polarity of electrodes 177 and 179 (E0-E15). Thus, indicator device 180 allows a clinician to visualize the electrical fields generated by each of electrodes 177 and 179 and, more specifically, a selected energy amplitude level as well as the polarity for each of electrodes 177 and 179. As a result, a clinician may utilize trial stimulation system 170 to assist in selecting programs that effectively treat the symptoms of the patient rather than selecting programs by trial and error. A clinician may also utilize trial stimulation system 170 when placing leads 176 and 178 within a patient because the electric fields generated by electrodes 177 and 179 carried by leads 176 and 178 are affected, particularly for cross stimulation, as leads 176 and 178 are positioned relative to one another. Additionally, a clinician or a technician may utilize trial stimulation system 170 and, in particular, indicator device 180 to more efficiently troubleshoot or identify a problem when trial stimulation system 170 is not operating properly.

Further, trial stimulation system 170 may store the energy amplitude levels measured by indicator device 180. For example, indicator device 180 or trial stimulator 172 may store or archive measured energy amplitude levels for therapy delivered to a patient via leads 176 and 178. A clinician may examine the archived energy amplitude levels with feedback perceived form the patient to analyze the efficacy of the therapy to determine if the therapy was successful or optimize, improve, or tailor the therapy over time. In this case, indicator device 180, trial stimulator 172, or both may include means for displaying the archived energy amplitude levels. Preferably, the archived energy amplitude levels may be displayed via a pixelized display that presents a user interface that graphically represents the archived energy amplitude levels. For example, indicator device 180 may include memory to store the archived energy amplitude levels and a pixelized display that presents a user interface which graphically represents the archived energy amplitude levels Where trial stimulator 172 includes a pixelized display for graphically representing the archived energy amplitude levels, indicator device 180 may communicate the archived energy amplitude levels to trial stimulator 172 via cable or wire 190, such as a USB cable, a wireless connection, or removable optical or magnetic media.

In some embodiments, trial stimulator 172 may control electrical stimulation therapy delivered to the patient based on a comparison to values stored in memory. For example, indicator device 180 may measure energy amplitude levels in real-time and compare the measured energy amplitude levels to the values stored in memory. By comparing the measured energy amplitude levels to values stored in the trial stimulator, excessive or insufficient stimulation may be prevented from being delivered to a patient. As a result, therapy delivered to the patient may be better controlled thereby reducing the pain experienced by the patient.

Figure 7:
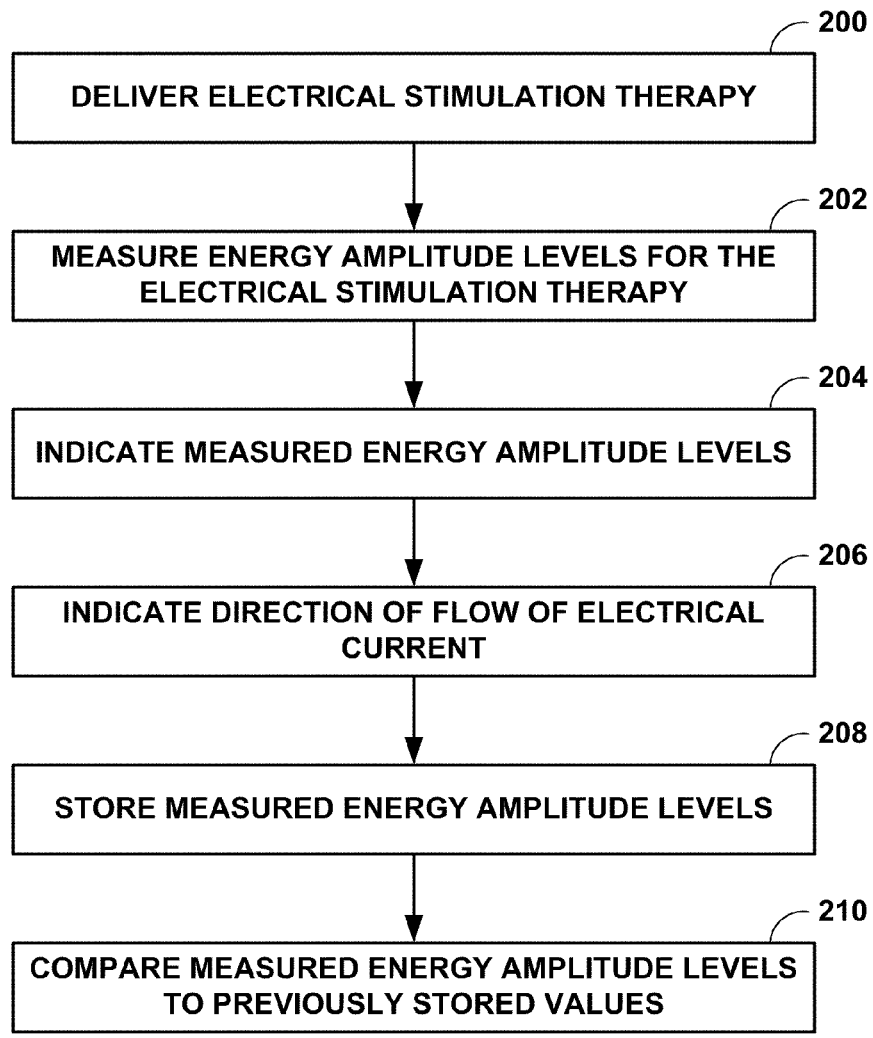
FIG. 7 is a flowchart illustrating a method that may be employed by an indicator device to measure and indicate energy amplitude levels delivered to an array of electrodes providing neurostimulation therapy to a patient during a trial period.

FIG. 7 is a flowchart illustrating operation of a trial stimulation system 170. Initially, trial stimulator 172 delivers electrical stimulation therapy (200) in the form of electrical pulses via electrodes 177 and 179 carried by leads 176 and 178. In particular, trial stimulator 172 generates electrical stimulation therapy in accordance with one or more selected programs. A clinician may interact with an external programmer to select the programs and adjust stimulation parameters for selected programs.

Indicator device 180 measures the energy amplitude levels for the electrical stimulation therapy (202) delivered by each of electrodes 177 and 179. Indicator device 180 is electrically connected in parallel with trial stimulator 172 and leads 176 and 178 and is designed to measure the energy amplitude levels without affecting the electrical stimulation therapy delivered to the patient. Indicator device 180 also concurrently indicates the measured energy amplitude levels (204) as well as indicate the direction of flow of current (206) or polarity in real-time for each of electrodes 177 and 179. As an example, indicator device 180 may concurrently indicate the power and electrical charge delivered per pulse via each of electrodes 177 and 179 carried by leads 176 and 178. As shown in FIG. 6, indicator device 180 may include an array of indicator lights, such as ten segment LED bar graphs 182 and 184, to indicate one or more measured energy amplitude levels for each of electrodes 177 and 179. Ten segment LED bar graphs 182 and 184 indicate the measured energy amplitude levels by activating a number of LEDs in proportion to the measured energy amplitude levels. Indicator device 180 also includes indicator lights 186 and 188 for indicating the direction of electrical current or polarity for each of electrodes 177 and 179. When one of electrodes 177 and 179 acts as a source, the corresponding one of indicator lights 186 and 188 may active a green LED. In contrast, when one of electrodes 177 and 179 acts as a sink, the corresponding one of indicator lights 186 and 188 may active a red LED. In alternative embodiments, indicator device 180 may include a pixelized display that presents a user interface to graphically represent the measured energy amplitude levels and polarity for each of electrodes 177 and 179.

Indicator device 180 or trial stimulator 172 may also store or archive measured energy amplitude levels (208) for therapy delivered to a patient via leads 176 and 178. A clinician may analyze the efficacy of the therapy by examining the archived energy amplitude levels with feedback perceived from the patient. Accordingly, indicator device 180, trial stimulator 172, or both may include means, such as a pixelized display, for displaying the archived energy amplitude levels. Where trial stimulator 172 includes a pixelized display for graphically representing the archived energy amplitude levels, indicator device 180 may communicate the archived energy amplitude levels to trial stimulator 172 via cable or wire 190, such as a USB cable, a wireless connection, or removable optical or magnetic media.

In addition, trial stimulator 172 may compare the measured energy amplitude levels to previously stored values (210) to control electrical stimulation therapy delivered to the patient. For example, trial stimulator 172 may adjust the electrical stimulation delivered to the patient based on a comparison of measured energy amplitude levels to previously stored preset or default values, such as threshold values. The stored values may generally define a range of values that define normal operation or may comprise threshold values that define excessive or insufficient energy amplitude levels. Consequently, when the measured energy amplitude levels are not within the range of normal operation, trial stimulator 172 may adjust the electrical stimulation delivered to the patient accordingly, i.e., increase the energy amplitude level when the measured levels are below the range defined by the threshold values and decrease the energy amplitude level when the measured levels are above the range. Comparing the measure energy amplitude levels to threshold values may prevent excessive or insufficient stimulation from being delivered to the patient. As a result, electrical stimulation delivered to patient may be better controlled thereby increasing the efficacy of the electrical stimulation delivered to patient and reducing the pain experienced by patient 20.

Figure 8:
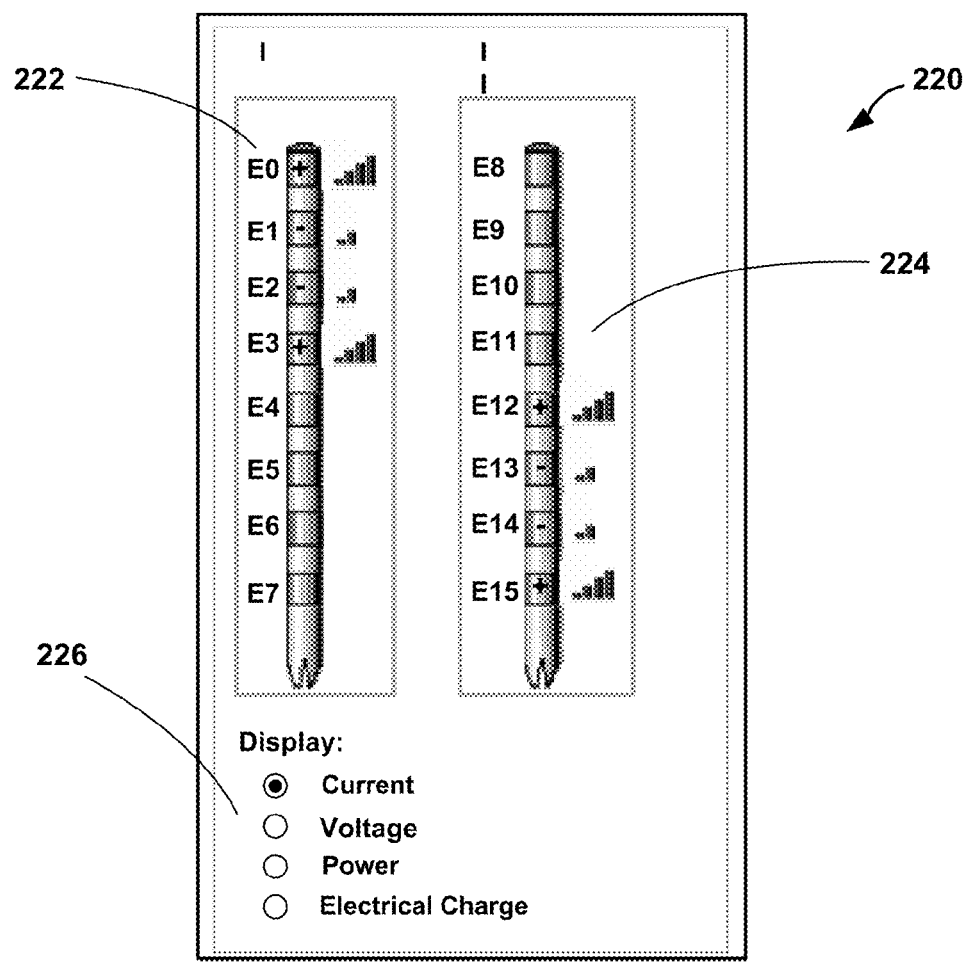
FIGS. 8 and 9 are diagrams illustrating example pixelized displays for graphically representing the measured energy amplitude levels delivered to an array of electrodes.
Figure 9:
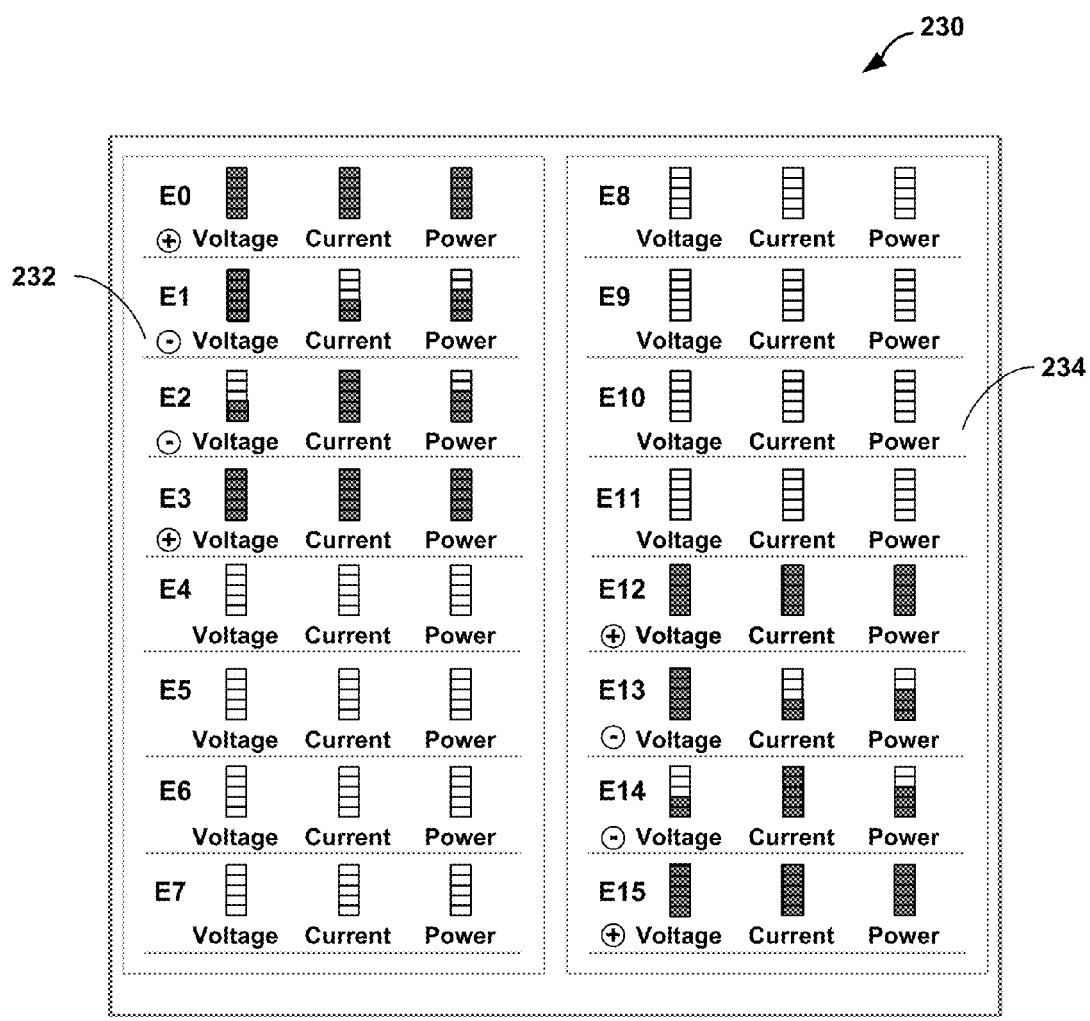

FIGS. 8 and 9 are diagrams illustrating example graphical user interfaces (GUI) 220 and 230, respectively, that may be provided by indicator device 180, trial stimulator 172, or both, to allow a clinician to visualize the electrical field generated by each of electrodes 177 and 179. Accordingly, a clinician may utilize trial stimulation system 170 to assist stimulation steering, lead placement, and trouble shooting. For example, a clinician may utilize trial stimulation system 170 to assist in selecting programs that effectively treat the symptoms of the patient, placing leads 176 and 178 within a patient, and troubleshooting or identifying a problem when trial stimulation system 170 is not operating properly. The configuration of and information displayed by GUIs 220 and 230 is merely exemplary and is provided for purposes of illustration.

FIG. 8 illustrates GUI 220 that may be used by a clinician to visualize the electrical fields generated by electrodes 177 and 179. GUI 220 may be presented via a pixelized display on indicator device 180, trial stimulator 172, or both. The measured energy amplitude levels for each of electrodes 177 and 179 may be graphically represented via windows 222 and 224, respectively. Electrodes 177A-H and 179A-H are labeled E0-E7 and E8-E15 in windows 222 and 224, respectively.

GUI 220 also includes a field 226 that allows a clinician to select which energy amplitude level or electrical characteristic of the stimulation therapy, such as electrical current, voltage, power delivered per stimulation pulse, and electrical charge delivered per stimulation pulse, to display. In the illustrated example, only one of electrical current, voltage, power, and electrical charge may be displayed. However, in alternative embodiments, GUI 220 may be designed to display more than one energy amplitude level of the electrical stimulation for each of electrodes 177 and 179.

As shown in FIG. 8, the current amplitude level as well as the polarity is displayed for each of electrodes 177 and 179. In particular, GUI 220 indicates that electrodes 177A-D and electrodes 179E-H are currently delivering electrical stimulation therapy. Electrodes 177E-H and electrodes 179A-D are not currently delivering therapy. GUI 220 indicates the amplitude of the measured current level via a vertical bar graph following each electrode and indicates the polarity of the electrode using a positive (+) and negative (−) sign. The positive sign indicates that the corresponding electrode acts as a source and the negative sign indicates that the corresponding electrode acts as a sink. In the illustrated example, electrodes 177A-D and electrodes 179E-H deliver substantially identical stimulation therapy, i.e., electrodes 177A, 177D, 179E, and 179H act as a source while delivering an electrical pulse with an amplitude corresponding to four vertical bars and electrodes 177B, 177C, 179F, and 179G act as a sink while delivering an electrical pulse with an amplitude corresponding to two vertical bars.

FIG. 9 illustrates GUI 230 that may be used by a clinician to visualize the electrical fields generated by electrodes 177 and 179. GUI 230 may be presented via a pixelized display on indicator device 180, trial stimulator 172, or both. The measured energy amplitude levels for each of electrodes 177 and 179 may be graphically represented via windows 232 and 234, respectively. Electrodes 177A-H and 179A-H are labeled E0-E7 and E8-E15 in windows 222 and 224, respectively. In contrast to GUI 220, GUI 230 simultaneously displays the electrical voltage, current, and power delivered per stimulation pulse for each of electrodes 177 and 179. However, in alternative embodiments, GUI 230 may also be capable of displaying the electrical charge delivered per stimulation pulse for each of electrodes 177 and 179. In any case, GUI 230 may generally allow a clinician to selectively display one more energy amplitude levels or electrical characteristics of the stimulation therapy.

As shown in FIG. 9, GUI 230 indicates that electrodes 177A-D and electrodes 179E-H are currently delivering electrical stimulation therapy and electrodes 177E-H and electrodes 179A-D are not currently delivering therapy. The amplitude of the measured electrical voltage, current, and power levels are indicated via a vertical bar graph following each electrode and indicates the polarity of the electrode using a positive (+) and negative (−) sign. The positive sign indicates that the corresponding electrode acts as a source and the negative sign indicates that the corresponding electrode acts as a sink. In the illustrated example, electrodes 177A-D and electrodes 179E-H deliver substantially identical stimulation therapy. Specifically, electrodes 177A, 177D, 179E, and 179H act as a source while delivering an electrical pulse with an amplitude corresponding to the maximum voltage and maximum current. Accordingly, electrodes 177A, 177D, 179E, and 179H deliver the electrical pulse with maximum power. Electrodes 177B and 179F act as sinks and deliver an electrical pulse with maximum voltage and current corresponding to two bars on the vertical bar graph. As a result, the power delivered by electrodes 177B and 179F is less than the maximum power and is illustrated as having power corresponding to two bars on the vertical bar graph in FIG. 9. Electrodes 177C and 179G also act as sinks and deliver an electrical pulse with the same power as electrodes 177B and 179F, i.e., but deliver the pulse with maximum current and a voltage corresponding to two bars on the vertical bar graph.

Various embodiments of the invention have been described. These and other embodiments are within the scope of the following claims.

The invention claimed is:

1. A method comprising:
   measuring energy amplitude levels associated with electrical stimulation therapy delivered from an electrical stimulation generator to an array of implanted stimulation electrodes carried by one or more leads via a measurement circuit; and
   indicating the measured energy amplitude levels delivered to one or more of the implanted electrodes within the array via a plurality of indicators, wherein each of the indicators corresponds to one of the electrodes, and the indicators are physically arranged to substantially correspond to the array of implanted stimulation electrodes carried by the one or more leads.

2. The method of claim 1, wherein the energy amplitude levels includes at least one of electrical voltage levels, electrical current levels, power levels, and electrical charge levels.

3. The method of claim 1, further comprising updating the measured energy amplitude levels and indicating the updated energy amplitude levels on a periodic basis.

4. The method of claim 1, wherein indicating includes, for each of the electrodes, activating a number of indicator lights within an array of indicator lights in proportion to the measured energy amplitude levels in real-time.

5. The method of claim 1, wherein the measurement circuit is placed in series with the electrical stimulation generator and the array of stimulation electrodes.

6. The method of claim 1, wherein indicating the measured energy amplitude levels includes simultaneously indicating the measured energy amplitude levels for each of the electrodes within the array.

7. The method of claim 1, wherein the electrical stimulation generator comprises an external electrical stimulation generator.

8. The method of claim 1, wherein the electrical stimulation generator comprises an implantable electrical stimulation generator.

9. An external indicator device comprising:
   an external device housing; and
   a plurality of indicators, carried by the external device housing, that indicate measured energy amplitude levels delivered from an electrical stimulation generator to an array of implanted stimulation electrodes carried by one or more leads, wherein the energy amplitude levels are measured via a measurement circuit,
   wherein each of the indicators corresponds to one of the electrodes, and the indicators are physically arranged to substantially correspond to the array of implanted stimulation electrodes carried by the one or more leads.

10. The device of claim 9, wherein the energy amplitude levels include at least one of electrical voltage levels, electrical current levels, power levels, and electrical charge levels.

11. The device of claim 9, wherein the indicators indicate updated energy amplitude levels measured by the measurement circuit on a periodic basis.

12. The device of claim 9, wherein respective indicators include an array of indicator lights, and the indicator activates a number of indicator lights within the array of indicator lights in proportion to the measured energy amplitude level in real-time.

13. The device of claim 9, wherein the measurement circuit is placed in series with the electrical stimulation generator and the array of stimulation electrodes.

14. The device of claim 9, wherein the indicators simultaneously indicate the measured energy amplitude levels for each of the electrodes within the array.

15. The device of claim 9, wherein the electrical stimulation generator comprises an external electrical stimulation generator.

16. The device of claim 9, wherein the electrical stimulation generator comprises an implantable electrical stimulation generator.

17. A system comprising:
   an electrical stimulation generator that generates stimulation energy associated with electrical stimulation therapy;
   an array of implantable stimulation electrodes coupled to the electrical stimulation generator and carried by one or more leads;
   a circuit to deliver the stimulation energy to selected electrodes within the array of electrodes;
   a measurement circuit that measures energy amplitude levels of the stimulation energy delivered from the electrical stimulation generator to the implantable electrodes; and
   a plurality of indicators that indicate the measured energy amplitude levels delivered to respective electrodes within the array,
   wherein each of the indicators corresponds to one of the electrodes, and the indicators are physically arranged to correspond to the array of implantable stimulation electrodes carried by the one or more leads.

18. The system of claim 17, wherein the energy amplitude levels include at least one of electrical voltage levels, electrical current levels, power levels, and electrical charge levels.

19. The system of claim 17, wherein the measurement circuit updates the measured energy amplitude levels, and the indicators indicate the updated energy amplitude levels on a periodic basis.

20. The system of claim 17, wherein respective indicators include an array of indicator lights, and the indicator activates a number of indicator lights within the array of indicator lights in proportion to the measured energy amplitude level in real-time.

21. The system of claim 17, wherein the measurement circuit is placed in series with the electrical stimulation generator and the array of stimulation electrodes.

22. The system of claim 17, wherein the indicators simultaneously indicate the measured energy amplitude levels for each of the electrodes within the array.

23. The system of claim 17, wherein the electrical stimulation generator comprises an external electrical stimulation generator.

24. The system of claim 17, wherein the electrical stimulation generator comprises an implantable electrical stimulation generator.

25. A system comprising:
   means for measuring energy amplitude levels associated with electrical stimulation therapy delivered from means for generating electrical stimulation signals to an array of implanted stimulation electrodes carried by one or more leads; and
   means for indicating the measured energy amplitude levels delivered to one or more of the implanted electrodes within the array, wherein the means for indicating comprises a plurality of indicators, wherein each of the indicators corresponds to one of the electrodes, and the indicators are physically arranged to substantially correspond to the array of implanted stimulation electrodes carried by the one or more leads.

26. The system of claim 25, wherein the means for generating electrical stimulation signals comprises an electrical stimulation generator.

27. The system of claim 26, wherein the electrical stimulation generator includes one of an external electrical stimulation generator, and an implantable electrical stimulation generator.

28. The system of claim 25, wherein the one or more leads comprises one or more percutaneously implanted leads.

29. The system of claim 25, wherein the means for measuring the energy amplitude levels comprises a measurement circuit.

30. The system of claim 25, wherein the means for measuring energy amplitude levels is in an external device housing, the external device housing including a first electrical connection from the means for measuring energy amplitude levels to the means for generating electrical stimulation signals and a second electrical connection from means for measuring energy amplitude levels to the implanted electrodes.

31. The system of claim 25, wherein the means for measuring energy amplitude levels updates the measured energy amplitude levels, and the indicators indicate the updated energy amplitude levels on a periodic basis.

32. The system of claim 25, wherein respective indicators include an array of indicator lights, and the indicator activates a number of indicator lights within the array of indicator lights in proportion to the measured energy amplitude level in real-time.

33. The system of claim 25, wherein the means for measuring the energy amplitude levels is placed in series with the means for generating electrical stimulation signals and the array of stimulation electrodes.

34. The system of claim 25, wherein the indicators simultaneously indicate the measured energy amplitude levels for each of the electrodes within the array.

* * * * *